(12) United States Patent
Nakamura et al.

(10) Patent No.: US 6,527,922 B2
(45) Date of Patent: Mar. 4, 2003

(54) ELECTROLYZER

(75) Inventors: Shinichi Nakamura, Osaka (JP);
Kunihiko Fukuzuka, Osaka (JP);
Kenji Nagayoshi, Osaka (JP); Masaki Miyashita, Osaka (JP)

(73) Assignee: Omega Co. Ltd., Osaka (JP)

( * ) Notice: Subject to any disclaimer, the term of this patent is extended or adjusted under 35 U.S.C. 154(b) by 127 days.

(21) Appl. No.: 09/752,773

(22) Filed: Jan. 3, 2001

(65) Prior Publication Data

US 2002/0005361 A1 Jan. 17, 2002

(30) Foreign Application Priority Data

Jun. 6, 2000 (JP) ......................................... 2000-168678

(51) Int. Cl.$^7$ ................................................. C23B 1/34
(52) U.S. Cl. ................................... 204/272; 204/297.15
(58) Field of Search ................................ 205/501, 742, 205/556; 204/272, 297.15

(56) References Cited

U.S. PATENT DOCUMENTS 2,873,236 A * 2/1959 Ferris .......................... 205/501
5,753,098 A * 5/1998 Bess, Jr. et al. ............. 205/501

* cited by examiner

Primary Examiner—Arun S. Phasge
(74) Attorney, Agent, or Firm—Rader, Fishman & Grauer PLLC

(57) ABSTRACT

Barrel-shaped anodes and cathodes are alternately arranged in layers in a concentric manner with space between the electrodes. Anodes are ferrite poles with a long hole along the center axis or a pipe, and the hole is filled with a metal with a low melting point heated to the temperature at which it has some fluidity. Alternatively the hole is filled with mercury, which is a liquid at room temperature, and then a conductive metal terminal main body is inserted so that it has a sufficient contact area between the terminal and the ferrite electrode, resulting in improved conductivity at the contact point. Consequently, a compact electrolyzer with superior electrolysis performance that is long lasting, even if the electrical current per electrode area is increased, is achieved.

10 Claims, 7 Drawing Sheets

ELECTROLYZER

FIELD OF THE INVENTION

The present invention pertains to an electrolysis method and an electrolyzer wherein it is possible to create a sterilizing and cleansing water by electrolyzing a solution containing a halogen ion in order to sterilize and wash medical equipment, dishes, food, hands, etc.

BACKGROUND OF THE INVENTION

In the prior art, a platinized titanium electrode plate has been used as an electrode in order to create an electrolyte having a sterilizing and cleansing function, and in particular, it was used as an anode in a strongly acidic and strong acidifying environment. However, it has a problem in that it cannot withstand usage over a long period of time. From the point of view of having good anti-corrosivity, a nickel ferrite electrode (Japanese Laid-Open Patent Publication No. S53-9273/1978) has been used as a replacement. However, when the electric current is increased in order to improve the effect of the sterilization and cleansing, the terminal parts become hot, and consequently, the ferrite breaks due to thermal distortion, or the plastic case of the electrolytic reaction device became distorted due to thermal expansion.

With respect to above-mentioned ferrite, the present inventors have filed the patent applications which are published as Japanese Laid-Open Patent Publication Nos. 11-188364 and 11-309458. In the inventions disclosed in these publications, the present inventors achieved long lasting performance of electrodes that is three to five times longer, under the same conditions, than a conventional hand sterilizing or cleansing device with a platinum plated titanium electrode.

SUMMARY OF THE INVENTION

However, there was a problem such that when electric current applied to the electrode is further increased in order to obtain a greater sterilizing or cleansing effect, the temperature of a terminal part of the electrode increases. The increased temperature would cause deformation of a plastic case of the electrolyzer and leakage of electrolyte. In addition, in order for an electrolyzer to be simply installed in a home or hospital room, a small sized device that creates a sterilizing or cleansing solution was required. Downsizing of the electrolyzer further caused the risk of temperature raise of the terminal part.

In order to solve these problems, the object of the present invention is to provide an electrolyzer that is compact and long lasting capability and has superior electrolysis performance. Another object of this invention is to prevent the heat increase of a terminal part of an electrode when electric current applied is increased, even though the electrolyzer is in the small size. For these purposes, a nickel ferrite anode of an electrolyzer was improved so that thermal expansion and the deformation of the plastic case due to the overheating of the electrode were avoided along with the associated problem of liquid leakage. In addition, the entire shape of the electrolyzer was made into cylindrical so that it can form a durable structure.

Multiple anodes and cathodes are alternated in a concentric manner, with some space between the electrodes in a layer, so that the solution containing halogen ions between the electrodes is electrolyzed and sterilizing and cleansing water is created. For the anode, a nickel ferrite electrode was used because it is less expensive than platinum and it has a superior anti-corrosive property that is similar to platinum.

At the anode, halogen ions are precipitated as chlorine or bromine, and immediately a reaction is carried out with water. Then hydrochloric acid, etc., is created. Because it is in a strong acidic and strong acidifying environment, the anode is required to be a highly anti-corrosive electrode. Ferrite, which was selected based on its performance in the past, does not have high electrical conductivity, unlike regular metals, and it is hard and brittle due to it being ceramic. Therefore, it was difficult to connect the terminals using current methods such as welding. In the present invention, a sufficient contact area for the terminals and the ferrite electrodes is prepared so that the conductivity at the contact point is increased.

PREFERRED EMBODIMENTS OF THE INVENTION

Figure 1:
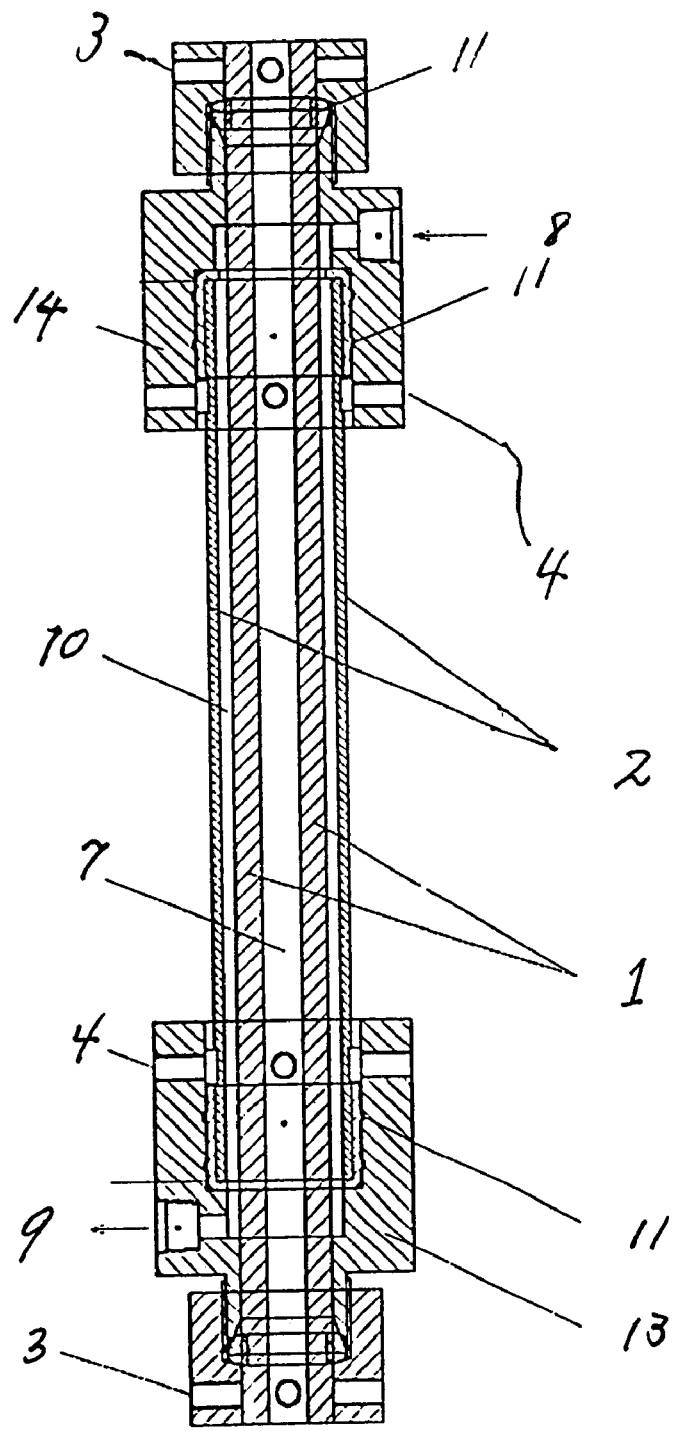
FIG. 1 is a cross-section of the electrolysis constituted with barrel-shaped anodes and cathodes of the present invention.
Figure 2:
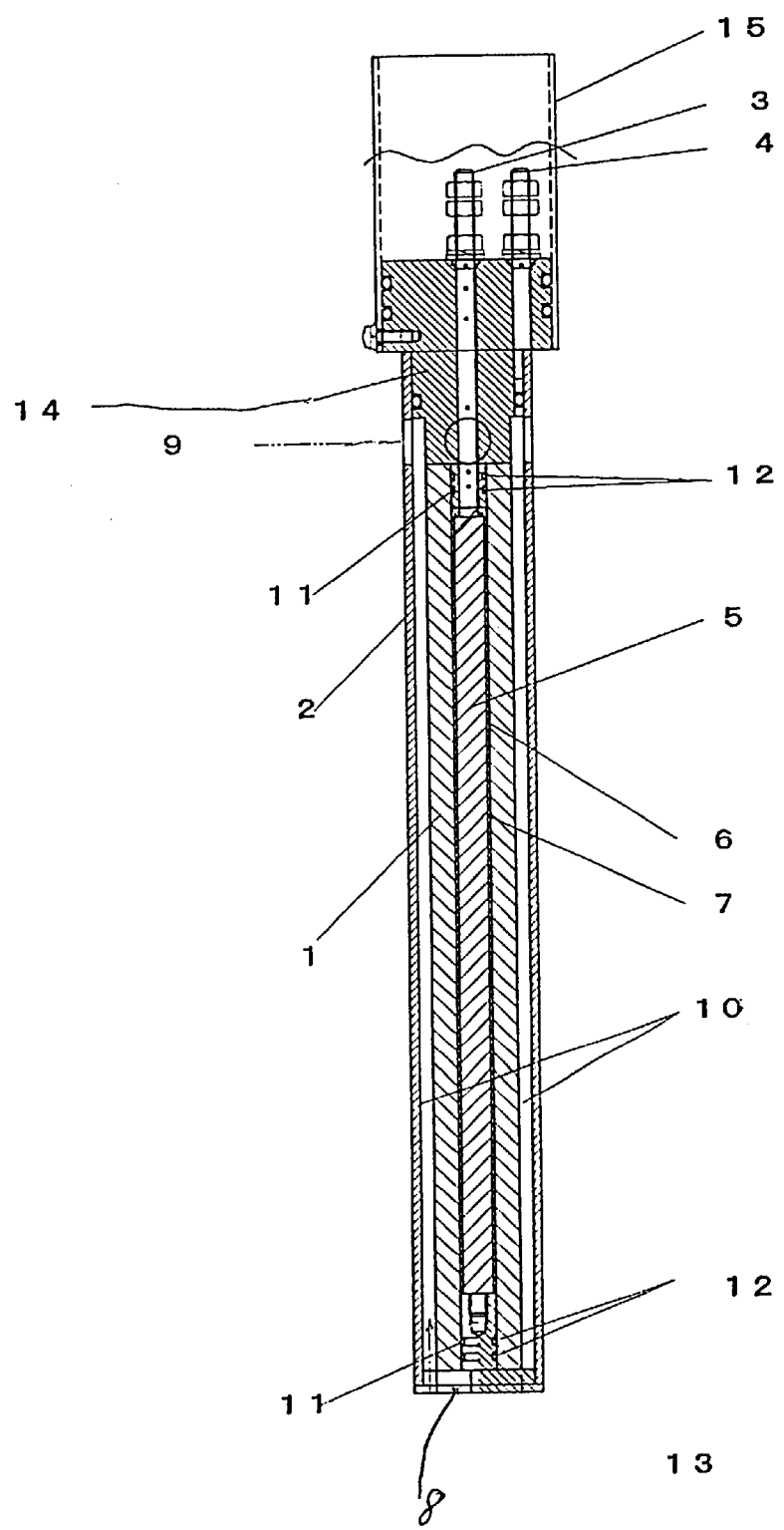
FIG. 2 is a cross-sectional view that displays the electrolyzer comprising a barrel-shaped anode and cathode of the present invention.

In the present invention, as shown in FIGS. 1 and 2, it is preferable that the anode 1, located at the most center location in the cylindrical structure, can be a ferrite pole having a long hole 7 in the direction of the center axis or can be a pipe. A terminal main body 5 that is a conductive metal pole having slightly smaller diameter than the diameter of the hole 7 is inserted into the hole 7. Between the circumference of the metal terminal main body 5 and the hole 7, a connection part 6 made of soft and conductive metal having a low melting point is completely filled in. The cathode 2, which is anti-corrosive metal pipe, is arranged in a concentric manner on the outer side of the long anode 1 with the distance between the electrodes being 0.5 to 5.0 mm.

The metal terminal main body 5 can be any material which is usually used as an electrical conductive material such as copper, gunmetal, brass, iron, stainless steel or titanium. The long hole 7 is drilled along the direction of the center axis of the ferrite anode pole 1 and is filled with the soft and conductive metal connection part 6 with a low melting point in advance. Then, said conductive metal pole terminal main body 5, having a threaded exterior, is screwed into it. Consequently, the long ferrite and the long metal pole terminal come in contact over a large area. In addition, there is a soft and conductive metal pipe with a low melting point filled in between. Therefore, by screwing the metal pole terminal main body in, the entire gap between the terminal and ferrite is filled, resulting in very good electrical conductivity from the terminal to the ferrite. Consequently, even when the electric current is increased, the voltage is not increased. In other words, it prevents abnormal heat from being generated at the terminal part.

When screwing the conductive metal pole terminal main body 5 in, if the soft and conductive metal with a low melting point, for instance an alloy with a low melting point from 80 to 180° C., is heated to the point where it becomes fluid, or if mercury, which is liquid at room temperature is used, the electrical conductivity from the terminal to the ferrite is further improved.

The electrolyzer is constituted in such way that the barrel-shaped anodes and cathodes are alternately arranged in a layer in a concentric manner with some space between the electrodes. The anode 1, which is located at the center-most location is a ferrite pole having a long hole 7 along the center axis or is a pipe. Said anode is filled with a soft and conductive metal pipe with a low melting point that has a thickness of 0.5 to 1 mm in advance. Then, conductive metal pole terminal main body 5 with its threaded exterior, which is slightly smaller than the opening is inserted. The metal pole terminal main body is screwed in and the gap between the circumference of the terminal and the opening is entirely filled with the soft and conductive metal. Consequently, inside the long pole shaped anode, the long terminal comes in contact with the ferrite over a large area, and therefore, a sufficient electrical current is conducted to the electrode at a low voltage. On the outer side of the long anodes, anti-corrosive metal pipes as cathodes are arranged in a concentric manner with a distance between the electrodes of 0.5 to 5.0 mm. A solution containing halogen ions is supplied to the area between the electrodes, and is then electrolyzed. As a result, a long lasting and compact electrolyzer that creates sterilizing and cleansing water is created.

When screwing the conductive metal pole terminal main body in, if the soft and conductive metal with a low melting point, is heated to the point where it becomes fluid, or if mercury, which is liquid at room temperature is employed, the electrical conductivity from the terminal to the ferrite is further improved and the voltage will not be increased when the electric current is increased. Consequently, abnormal heat at the terminal parts can be prevented, and a long lasting electrolyzer with a simple manufacturing process can be manufactured.

When a barrel-shaped ferrite pipe is used for the anode, a connecting terminal at the end of a long pipe does not provide sufficient electric conductivity. Therefore, two ferrite pipes with different diameters from 1 to 5 mm, and a conductive metal pipe with a diameter in between the two pipes and a thickness of around 1 mm, are layered in a coaxial manner. Then, in between, a low melting point metal, which is heated and melted, is injected and filled in. When this conductive metal pipe is used as the terminal main body and electrified, it is possible to pass an electrical current with a low resistance between the area to the inside and the area to the outside of the anodes, which are ferrite pipes.

In this case, cathodes, which are anti-corrosive conductive metal pipes are arranged on the inner side and outer side of the two layered anodes, which are ferrite pipes, with a distance between the electrodes of 0.5 to 5.0 mm, so that effective electrolysis can be conducted. By repeating the above in the same manner, a barrel-shaped electrolyzer with a multi-layer coaxial structure can be manufactured.

Figure 7:
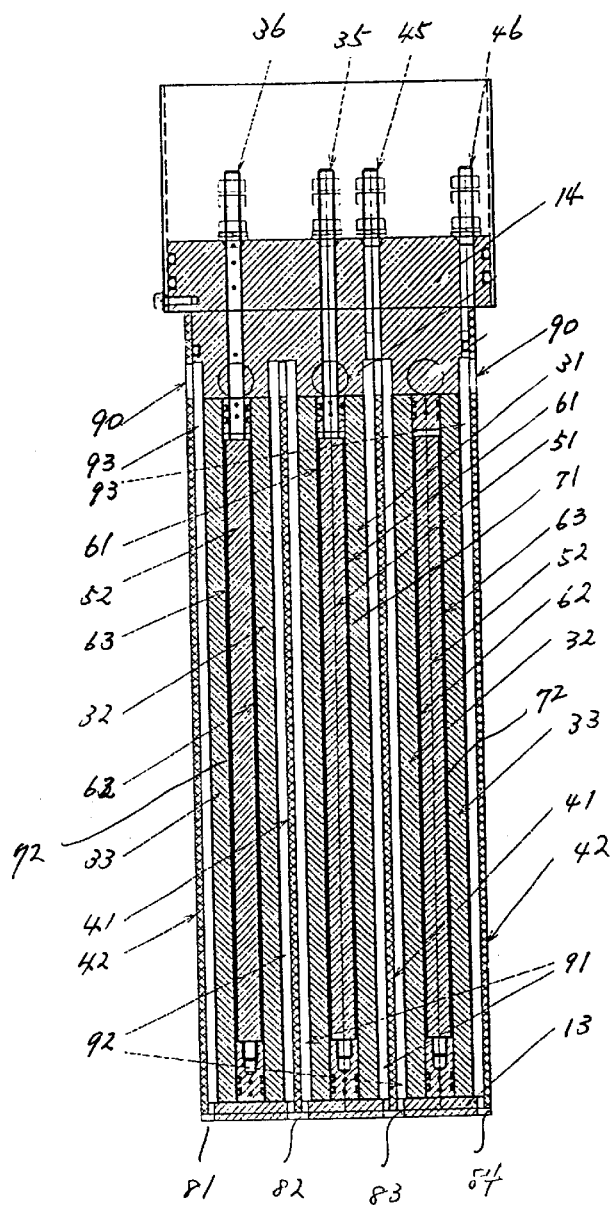
FIG. 7 is another cross-section of the electrolysis of the present invention constituted with plurality of barrel-shaped anodes and cathodes that are alternated in a concentric manner.
Figure 8:
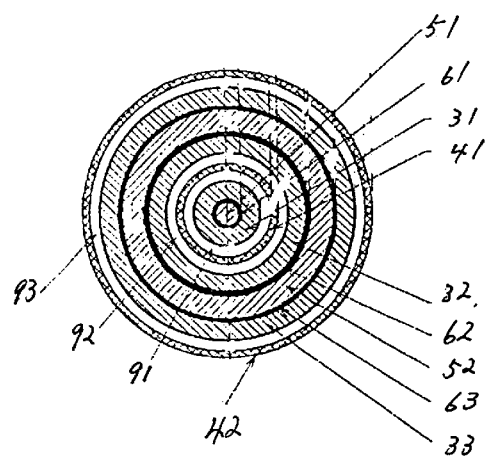
FIG. 8 is a cross-sectional view along the line VIII—VIII of FIG. 7.

As shown in FIGS. 7 and 8, barrel-shaped anodes @@ and cathodes may be alternately combined in a concentric manner to form an electrolysis. The electrolysis is arranged in such a way that the parts are at right angles to a container. In between the electrodes, a solution containing halogen ions is supplied. Electrolysis is carried out in such a way that the designated halogen concentration will be achieved. At this time, at reaction area 10, an electrolysis reaction is carried out and hypohalogen acid and activated oxygen are generated and then at the same time, hydrogen and oxygen are generated as a by-product at the surface of the electrodes, and they violently fizz and rise up. This rising of the bubbles, namely, the air lift allows the solution containing the halogen ions to be naturally drawn from opening 8, which is located at the bottom of the electrolyzer and then in the reaction area between the electrodes, electrolysis is carried out. Consequently, the generated sterilizing and cleansing water flows out from outlet 9 of the container to the outside.

Figure 4:
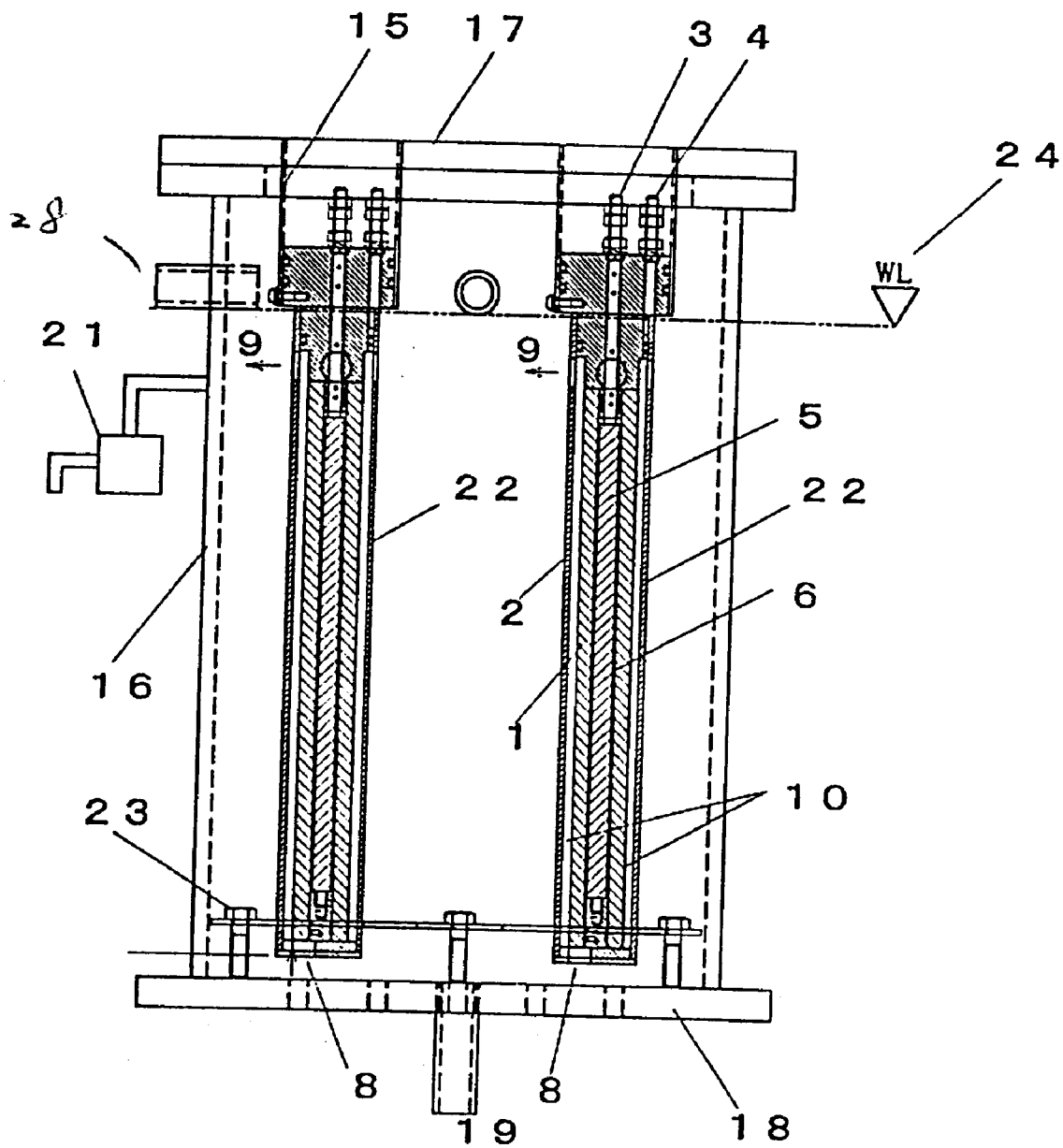
FIG. 4 is a cross-sectional view of a container having four sets of the electrolyzers of the present invention.

As shown in FIG. 4, the container 16 is filled with water containing halogen ions, and said electrolyzer is dipped in so that only the terminal cover 15 is above the water level. Then electrolysis is carried out. The water in the container, i.e., the solution containing halogen ions is naturally drawn from the inlet 8 located at the bottom of the electrolyzer due to the air lift, and then the sterilizing and cleansing water generated due to the electrolysis in the reaction area between the electrodes flows out from the outlet 9 to the outside. This is repeated and the concentration of the remaining halogen inside the container is gradually increased. Therefore, using the concentration sensor for the remaining halogen 21, the electrolysis is controlled so that the concentration of the remaining halogen in the water inside the container will be the predetermined level. Meanwhile, the generated sterilizing and cleansing water is discharged and at the same time, the solution containing halogen ions is supplied. Since there is an automatic control function as described above, it is possible to constantly create sterilizing and cleansing water with the desired halogen concentration.

Embodiments of the present invention are further described in detail below, with reference made to relevant accompanying drawings.

EXAMPLE 1

FIG. 1 is a cross-section of the electrolysis constituted with barrel-shaped anodes and cathodes.

In FIG. 1, the anode 1 is a nickel ferrite pipe (effective length of 280 mm, diameter of 28 mm, electrode area of 2.6 $dm^2$), and cathode 2 is a titanium pipe (effective length of 280 mm, internal diameter of 36 mm, electrode area of 2.6 $dm^2$). with the distance between the electrodes being 0.5 to 5.0 mm. In the present embodiment, a nickel ferrite pipe is employed for anode 1 and a titanium pipe is employed for cathode 2. However, in the case of a small capacity and low electrical current (5 amps or lower), a combination of a platinized titanium anode and a titanium cathode can be used. When multiple barrel-shaped anodes 1 and cathodes 2 are arranged in alternate layers in a concentric manner with space between the electrodes, the assembly process for the device is easier than for one that employs nickel ferrite.

In FIG. 1, water containing halogen ions is supplied from the opening inlet 8 to the reaction area 10 between the electrodes 1 and 2 and electrolyzed. Said water then becomes sterilizing and cleansing water, and flows outside from the outlet 9. When a mechanism to supply the electrolyte solution and a control mechanism are added, a compact and simple device that creates sterilizing and cleansing water can be achieved. It can be arranged both horizontally and vertically, so that by directly connecting said device to the faucet, it can used even in a small space.

Figure 5:
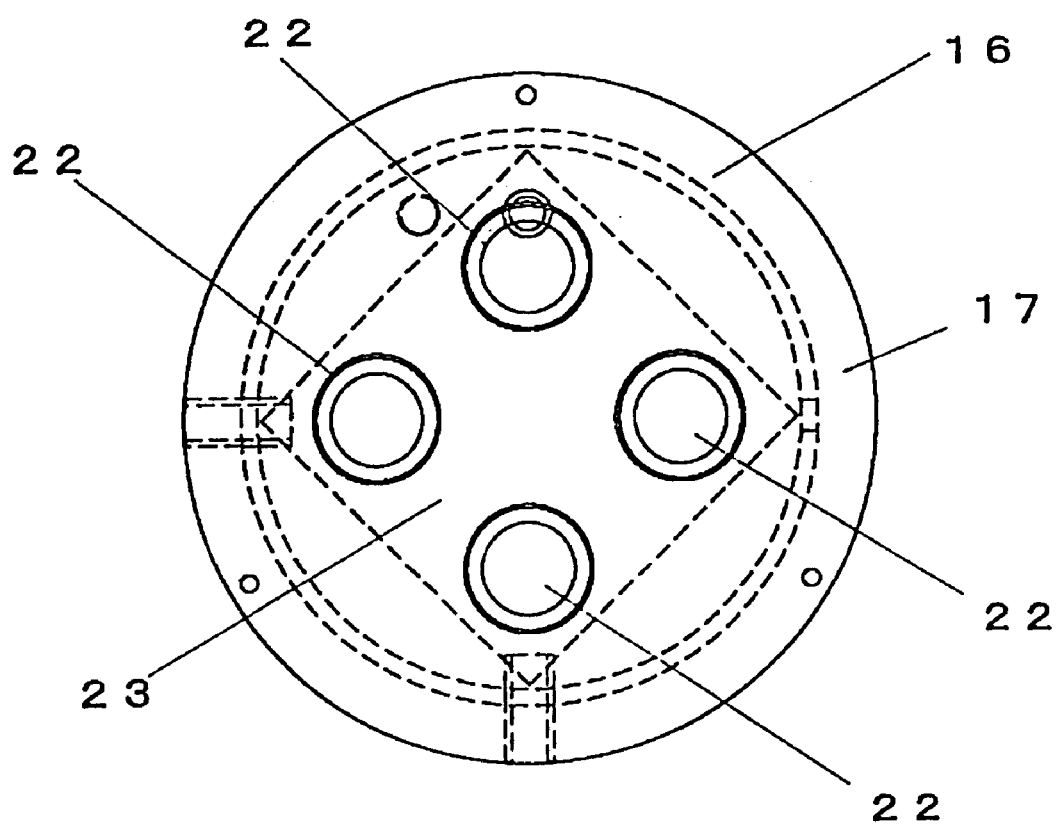
FIG. 5 is a planar top view of the electrolyzer device of the present invention.

The electrical conductivity of the nickel ferrite pipe as the anode 1 was studied. As shown in FIG. 5 and Table 1, at 5 amps, the resistance of the nickel ferrite between 2 points along the length was significantly large, for example, 8.3 Ω at 100 mm, 12.0 Ω at 200 mm and 16.0 Ω at 300 mm. As shown in FIG. 1, by applying a total of 8 terminals that also serve as anchoring screws, with 4 terminals along the circumference near each of the ends of the nickel ferrite electrode, it was possible to achieve a resistance of 10 Ω for an electrical current of 5 amps at 300 mm.

Embodiment 2

FIG. 2 is a cross-sectional view that displays the electrolyzer comprising a barrel-shaped anode 1 and cathode 2. A terminal main body 5 and a metal connection part 6 having a low melting point are inserted into a long hole 7 of the anode 1. The anode 1 of the example of FIG. 2 is a nickel ferrite barrel with a diameter of 28 mm, a thickness of 8 mm, a length of 280 mm, and on its exterior, with a distance between electrodes of 4 mm, is placed cathode 2, which is a SUS316L pipe with a diameter of 28 mm, a thickness of 3 mm, an electrode length of 280 mm, and a total length of 325.1 mm. The first and second electrode anchors 13 and 14 respectively are made of non-conductive material and is placed at the bottom and top of the electrodes respectively. The first electrode anchor 13 has an opening 8 for supplying a solution containing halogen ions. The second electrode anchor 14 and cathode 2 form an outlet 9 for the electrolyte sterilizing and cleansing water. O-rings 12 are used to seal the ends of the anode hole at the sealing parts 11.

In this embodiment a ferrite pipe which is extruded and then sintered was used as anode 1. Then, soft and conductive metal connection part 6 with a low melting point are inserted into the hole 7 of the anode 1 in advance. The terminal main body 5, which has an anode terminal 3 on the top portion, is forced in and attached. As a metal with a low melting point, lead (melting point of 327 C), Wood's metal (melting point of 73 C, Bi50, Pb25, Sn13, Cd12) and mercury (liquid at room temperature) can be used. The electrical resistance for these metals is 20.8×10$^{-6}$ Ω/cm for lead, 31.3 ×10$^{-6}$ Ω/cm for Wood's metal, and 98.4×10$^{-6}$ Ω/cm for mercury. Nickel ferrite has a high resistance of 0.25 Ω/cm.

A rolled up thin plate of lead and Wood's metal with a thickness of 1 mm was inserted inside the nickel ferrite pipe so that it adheres. Then, the nickel ferrite pipe was heated to near its melting point and it was softened. Next, terminal main body 5, which is a SUS304, was inserted in a slow screwing manner and became fixed. The electrical resistance of the SUS304 was 72×10$^{-6}$ Ω/cm. Not only with Wood's metal, but also in the case of lead, when the terminal main body 5 is formed with threads, said terminal main body can be inserted without being heated, with adequate adhesion. However, with heating, better results were achieved.

Mercury is liquid at room temperature so that inside the long hole 7 in the ferrite, which has its bottom portion closed with the first electrode anchor 13 and O-rings 12, 15 ml of mercury is poured in advance. Then, from the top, a terminal main body 5 with anode terminal 3 is carefully inserted. The mercury has sufficiently filled the gap between the terminal and the ferrite and any extra flows up. However, this extra mercury is stored in the space located on the top end of the terminal and the O-rings 12 of the second electrode anchor 14. Then the top portion of this anode was sealed with the second electrode anchor 14 and O-rings 12 and then the electrical resistance of the anode was measured in the same manner as in Embodiment 1.

Figure 3A:
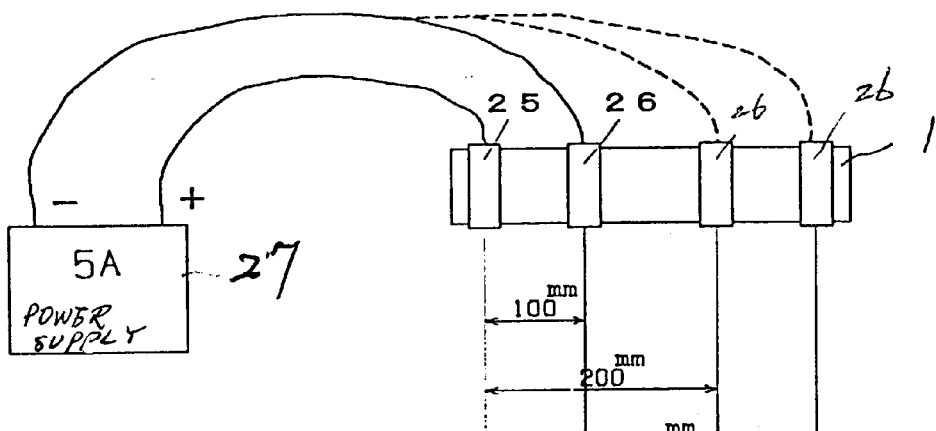
FIGS. 3A to 3C are explanatory diagrams to show the method of measurement.
Figure 3B:
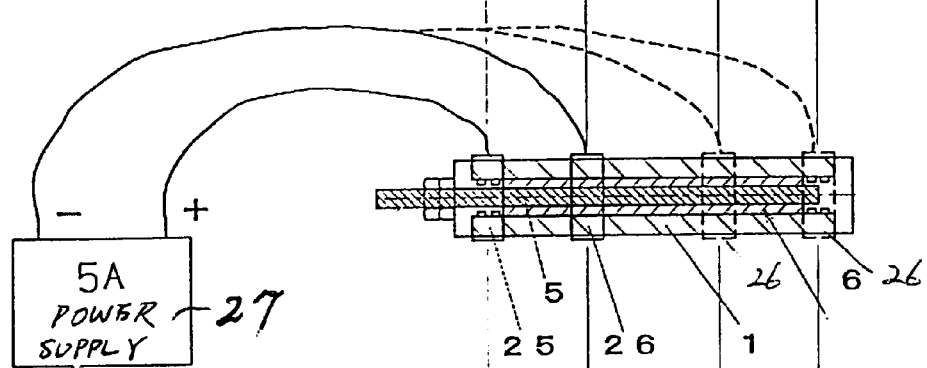
Figure 3C:
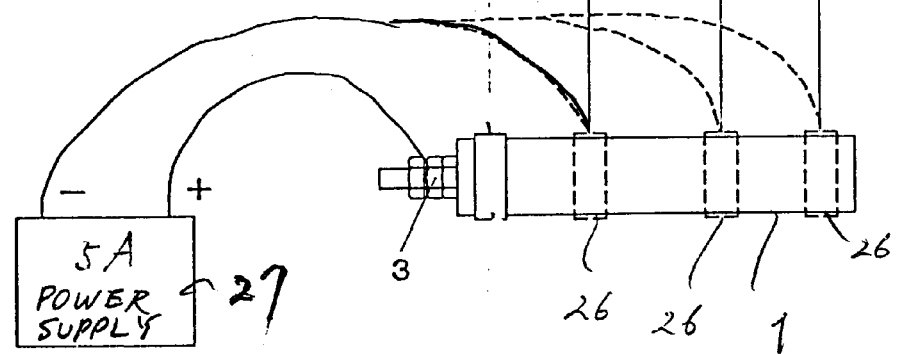

FIGS. 3A, 3B, and 3C show the method of an experiment that studies the changes in voltage of the electrical current, based on the different locations and connections of the nickel ferrite anode and the terminal.

FIG. 3A shows the method of measurement of the voltage by conducting an electrical current of 5 amps between two points 25 and 26 on the surface of the barrel-shaped nickel ferrite anode 1.

FIG. 3B is a cross-sectional view that shows the method of measurement of the voltage by conducting an electrical current of 5 amps between two points 25 and 26 on the surface of the barrel-shaped anode 1, which is the nickel ferrite anode pipe filled with the metal connecting part 6 having a low melting point and the terminal main body 5.

FIG. 3C shows the method of measurement of the voltage by conducting an electrical current of 5 amps between two points, namely the terminal 3 and the points 26 on the surface of the barrel in which a nickel ferrite anode barrel is filled with 50 ml of mercury, in advance, before terminal main body 5 is inserted (examples 2-5 and 3-2 in Table 1).

As shown in FIG. 3B, as the metal conducting part 6, lead, Wood's metal, and mercury which are conductive metals with low melting points, are filled in between the nickel ferrite anodes 1 and terminals main body 5. As shown in FIGS. 3A through 3C, two points on the surface of the nickel ferrite anodes 1 and a power source 27 are connected with wire and the electrical current is supplied. One point 25 is fixed and the other point 26 can have its location changed so that a distance of 100 mm, 200 mm and 300 mm for the electrical current can be established. Then, an electrical current of 5 amps is generated by the electric source 27 and the resistance between the two points is measured.

Table 1 shows the results of the experiments. As a comparative example 1, only the ferrite was used as the anode 1 and no connecting metal part 6 was applied. Examples 2-1 thorough 2-5 are the cases of FIG. 3B and Examples 3-1 and 3-2 are the cases of FIG. 3C.

As is clear in Table 1, the electrical resistance is large as to the comparative example 1 when only ferrite is used as the anode 1. Therefore, as the distance increases for the electrical current, the resistance becomes larger and electrolysis becomes more difficult as for the comparative example 1. In all other examples 2-1 through 2-5 and 3-1 and 3-2 of Table 1 that employed lead, Wood's metal or mercury, the difference of resistance measured was greatly decreased and there was little influence from the distance the electrical current flowed. In addition, when said metals for the metal connecting part 6 were heated to near their melting point before the terminal main body 5 was inserted as for examples 2—2, 2-4 and 3-1, the results were further improved. In the case of examples 2-5 and 3-2 where mercury is used, because it is a liquid in the room temperature, the narrow gaps between the terminal main body 5 and the barrel-shaped anode 1 are filled without the mercury being heated. Therefore, the best results were obtained from among these tests. The main body of the electrolyzer is achieved when a pipe of USU316L, as the cathode pipe, is placed outside of anode 1 with the distance between the electrodes of 4 mm and the anode and cathode are fixed with the second electrode anchoring portion 14.

TABLE 1

Voltage of nickel ferrite electrode at an electrical current of 5 amps.

| Distance to be electrified | | 100 mm | 200 mm | 300 mm |
|---|---|---|---|---|
| Comparative Example 1 | Ferrite only is used | 8.3 | 12.0 | 16.0 |
| Example 2-1 | Ferrite and lead are used | 7.3 | 8.2 | 9.5 |
| Example 2-2 | Ferrite and lead are used and heated | 7.1 | 7.5 | 7.8 |
| Example 2-3 | Ferrite and Wood's metal are used | 6.5 | 6.6 | 6.8 |
| Example 2-4 | Ferrite and Wood's metal are used and heated | 6.2 | 6.2 | 6.3 |
| Example 2-5 | Ferrite and mercury are used | 6.0 | 6.0 | 6.1 |
| Example 3-1 | Ferrite and Wood's metal are used and heated | 2.8 | 2.9 | 2.9 |
| Example 3-2 | Ferrite and mercury are used | 2.4 | 2.4 | 2.6 |

Embodiment 3

FIG. 4 is a cross-sectional view of a container 16 having four sets of the electrolyzers 22 supported on a supporting member 23 as shown in FIG. 5, even though FIG. 4 shows two electrolyzers in cross-section. The water is introduced into the container 16 from the lower opening 19. The container 16 comprises a top part 17, a bottom part 18, a solution inlet 19 for introducing water solution that contains halogen ions therein, a discharge outlet 28 which discharges the sterilizing and cleansing water and a sensor 21 that senses halogen density or concentration in the solution water. Other parts in FIG. 4 denoted with the same numbers in other Figures are the same as those shown in those other Figures.

Figure 6:
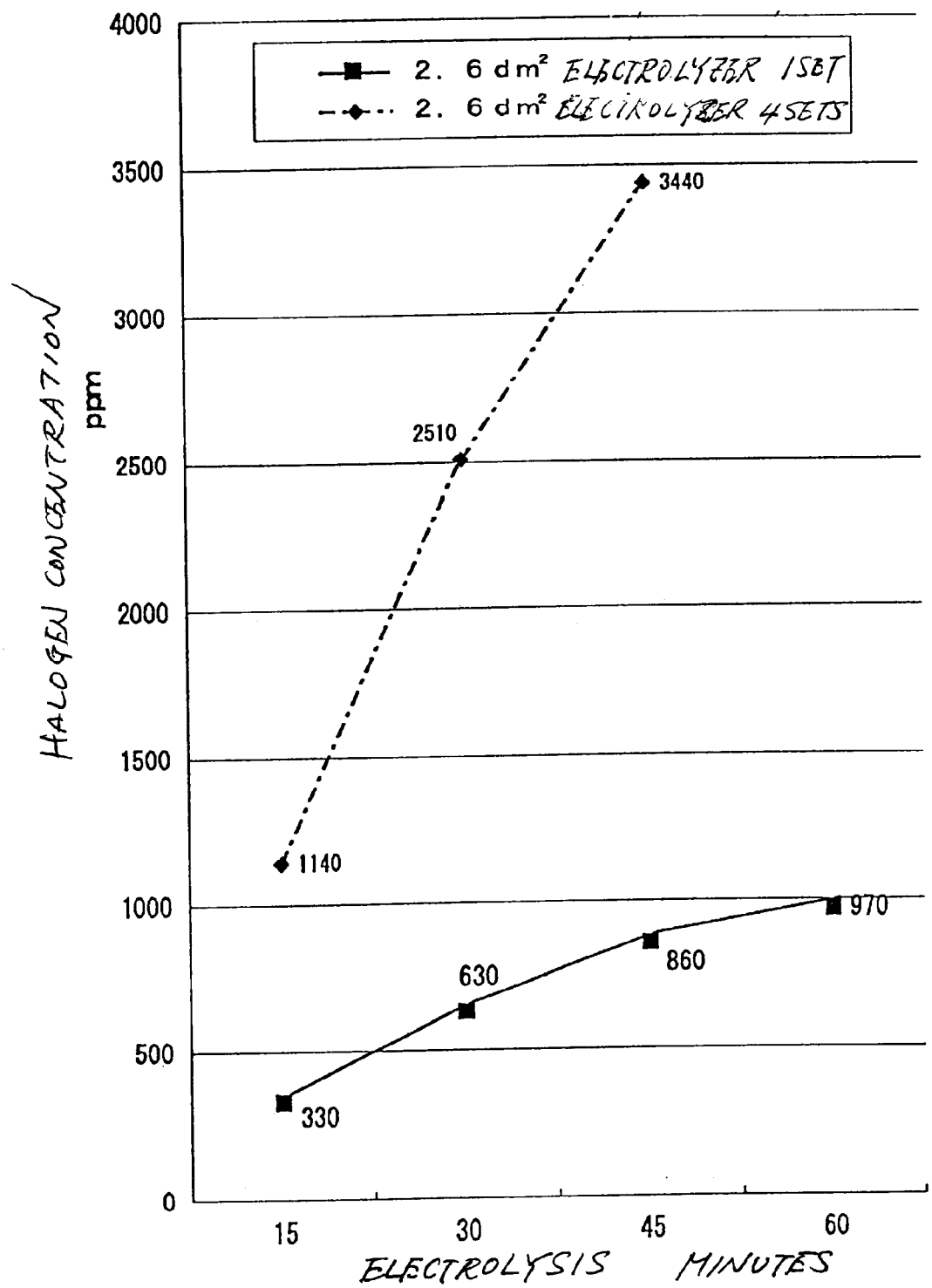
FIG. 6 is a graph that shows the results of the correlation between the electrolysis period and the halogen (chlorine) concentration for the device of the present invention.

The water used for the solution contains halogen ions. In this embodiment, 16 liters of 2.5% saline (electrical conductivity of 49,000 $\mu$S/cm) as water containing halogen ions is filled up to the predetermined water level (WL) 24. Then the electrolysis was carried out using 15 amps. Every 15 minutes an electrical current, voltage and the remaining chlorine concentration were measured and the results are shown in FIG. 6.

The water is introduced into the reaction area 10 of each of the electrolyzers 22. The reaction area is between the anodes and cathodes and allows the water to flow upward by means of air generated by electrolysis. The water is discharged from the outlet 9 and returned to the reaction area 10 from the inlet opening 8 whereby a higher concentration of hypochlorine acid or an abundance of active oxygen due to the electrolysis reaction is obtained. This circulation is repeated until it reaches the designated remaining halogen concentration sensed by the sensor 21. When the remaining halogen concentration or density of hypochlorine acid reaches predetermined value, an automatic control system (not shown) supplies a new solution containing halogen ions, and the sterilizing and cleansing water is discharged from the outlet 28.

The present example was conducted for the purpose of creating 16 liters of sterilizing and cleansing water with a high concentration of remaining chlorine in a short period of time in order to sterilize medical equipment, hospital sheets, etc. The cases of operating only one set and for operating four sets of electrolyzers 22 with 2.6 dm$^2$ of anode area were measured. In the case of one set used for 30 minutes the result was 630 ppm. In the case of 4 sets it was 2510 ppm.

FIG. 5 is a planar top view of the electrolyzer device that creates sterilizing and cleansing water shown in FIG. 4.

FIG. 6 is a graph that shows the results of the correlation between the electrolysis period and the halogen (chlorine) concentration for the device that creates sterilizing and cleansing water with one set and four sets of electrolyzers with 2.6 dm$^2$.

Embodiment 4

FIG. 7 is another cross-section of the electrolysis of the present invention constituted with plurality of barrel-shaped anodes and cathodes that are alternated in a concentric manner. FIG. 8 is a cross-sectional view along the line VIII—VIII of FIG. 7.

In this embodiment, a first barrel shaped anode 31 is located at the most center location in the cylindrical structure, and a second barrel shaped internal and external anode 32, 33 is arranged outside of the first anode 31 in a concentric manner. The first anode 31 is a ferrite pole having a long hole 71 in the direction of the center axis or is a pipe. A first terminal main body 51 that is a conductive metal pole having slightly smaller diameter than the diameter of the hole 71 is inserted into the hole 71. The first terminal main body 51 is connected to a first anode terminal 35. Between the circumference of the first terminal main body 51 and the hole 71, a connection part 61 made of soft and conductive metal having a low melting point is completely filled in. The second internal and external anode 32, 33 consists of a barrel shaped ferrite internal anode 32 and another barrel shaped ferrite external anode 33. Between the internal and external anodes, a cylindrical long hole 72 is formed. A second terminal main body 52 that is a barrel shaped conductive metal pipe having slightly larger inner diameter than the outer diameter of the internal anode 32 and slightly smaller outer diameter than the inner diameter of the external anode 33. The second terminal main body 52 is connected to a second anode terminal 36. Between the inner and outer circumference of the second terminal main body 52 and the hole 72, a connection parts 62 and 63 made of soft and conductive metal having a low melting point is completely filled in.

A first cathode 41, which is anti-corrosive metal pipe, is arranged in a concentric manner on the outer side of the first anode 31 and the inner side of the second internal anode 32 with the distance between the electrodes being 0.5 to 5.0 mm respectively. The first cathode 41 is connected to the first cathode terminal 45. A second cathode 42, which is also anti-corrosive metal pipe is arranged in a concentric manner on the outer side of the second external anode 33 with the distance between the electrodes being 0.5 to 5.0 mm. The second cathode 42 is connected to the second cathode terminal 46.

In FIG. 7, water containing halogen ions is supplied from the opening inlets 81, 82, 83, 84 to the reaction areas 91, 92, 93 between the electrodes 31 and 41, 41 and 32, and 33 and 42 for being electrolyzed. Said water then becomes sterilizing and cleansing water, and flows outside from the outlet 90. The first and second electrode anchors 13 and 14 respectively are made of non-conductive material and is placed at the bottom and top of the electrodes respectively. The first electrode anchor 13 has the openings 81 through 84 for supplying a solution containing halogen ions. The second electrode anchor 14 and the second cathode 42 form an outlet 90 for the electrolyte sterilizing and cleansing water.

The present invention has the above mentioned structure and produces the following effects.

(a) In accordance with the present invention, barrel-shaped electrodes, namely anodes and cathodes, are arranged in layers in an alternating concentric manner and they are compact and have a durable structure. In addition, the case made of vinyl chloride is barrel-shaped with a simple structure and is durable. Therefore, there is no leakage from an electrolyzer that is used over a long period of time. Moreover, as shown in FIG. 2, when the electrolyzer is attached with all the terminals on the top end so that the terminal cover 5 remains over the water level, it then, without being contained in a durable case, can be installed directly in the target water container. Consequently, the heat of the electrodes is absorbed by the water and they are cooled. The water in the container is drawn into the electrode due to the fizzing and rising of the air generated in the reaction area between the electrodes 10, namely the air lift, and said water is electrolyzed and exits. Therefore, without a pump, water inside the container is automatically circulated and electrolyzed. Consequently, the concentration of the remaining chlorine can be increased.

(b) In accordance with the present invention, it was possible to increase the conductivity because the terminal main body 5 and the metal connection portion with a low melting point 6 by having them come in contact and connect to the nickel ferrite over a large area. Although it has a high anti-corrosivity, the relative resistance is 0.25 $\Omega$/cm. It was possible to overcome the weak points of nickel ferrite, which is difficult to employ as an electrode with a large capacity, because the resistance is significantly higher compared to copper, platinum, lead, etc., which are on the order of $10^{-6}$ $\Omega$/cm, and which are normally used as electrodes. For alloys with low melting points, the melting point can be arbitrarily selected by changing the composition. Wood's metal has a melting point of 73° C. and it is solid at room temperature. However, in rare cases, a gap is generated with the ferrite and that portion will create heat. Then, the metal melts and fills the gap. Consequently, the resistance decreases and normal electrolysis continues.

(c) In accordance with the present invention, the long hole drilled in the direction of the axis in the pole of ferrite or in the ferrite pipe is filled with a metal pipe with a low melting point 6 in advance. Then, the conductive metal pole terminal main body 5, which is formed with threads, is screwed in. Consequently, the gap between the terminal main body and the ferrite is filled with the metal with a low melting point, resulting in a better connection.

(d) In accordance with the present invention, conductive metal with a low melting point, which becomes liquid through heating, or mercury, which is already liquid, fills the gap between the terminal main body and the nickel ferrite, resulting in better conductivity from the terminal main body to the nickel ferrite.

(e) In accordance with the present invention, when multiple barrel-shaped anodes are used in a concentric manner, for the anode 1, which is located directly at the center, the terminal can be connected in accordance with the invention described in claim 1. However, nickel ferrite anodes, which are located on the outer side of it, cannot be used in the same manner. Therefore, two nickel ferrite anodes with different diameters are placed in layers. Then, terminal main body 5, which is a barrel-shaped conductive metal is inserted in between. A barrel-shaped anode, which has a unified nickel ferrite anode and a terminal main body, with a conductive metal with a low melting point or mercury is constructed. Then, barrel-shaped cathodes are arranged, on its inner side and outer side, with the distance between the electrodes of 0.5–5.0 mm. By constructing anodes in this manner, not only are terminal connections over a much larger area assured, but also both the back and front side of the anode can be utilized.

(f) In accordance with the present invention, it is possible to manufacture long versions of ferrite poles or pipes of 30 cm or more or even over 1 meter using extrusion. With this invention, longer terminal main bodies allow longer electrodes to be manufactured. When these are used in a vertical fashion, an electrolyzer with an extremely small installation area can be designed and it is useful as a device that creates sterilizing and cleansing water in an ICU.

(g) In accordance with the present invention, a better result can be achieved because when the long ferrite electrode, described in the above (F) is employed, a better connection between the terminal main body and the long ferrite electrode is desired for conductivity.

(h) In accordance with the present invention, the electrolyzer can be directly placed inside a container for sterilizing and cleansing water. Therefore, it does not require extra pipes and can be installed in a small area. Water inside the container, which is for sterilizing and cleansing water circulates between the electrolyzers, due to the air lift, without a pump. Consequently, the concentration of the remaining halogen can be increased in an efficient manner. In this case, not only tap water or well water can be used as water containing halogen ions. Also, by appropriately adding halogen ions to bath water, pool water, fish culturing aquarium water, or waste water it is possible to sterilize the water.

(i) In accordance with the present invention, the concentration of the remaining halogen is measured with the concentration sensor 21 which senses concentration of remaining halogen and electrolysis is controlled with the concentration controller. Therefore, sterilizing and cleansing water with a given concentration is always available for sterilizing medical equipment or to prevent hospital infection.

The disclosure of Japanese Patent Application No. 11-2000-168578 filed Jun. 6, 2000 including specification, drawings and claims are herein incorporated by reference in its entirety.

Although only some exemplary embodiments of this invention have been described in detail above, those skilled in the art will readily appreciated that many modifications are possible in the exemplary embodiments without materially departing from the novel teachings and advantages of this invention. Accordingly, all such modifications are intended to be included within the scope of this invention.

What is claimed is:

1. An electrolyzer that creates sterilizing and cleansing water comprising a barrel-shaped anode and a barrel shaped cathode, wherein said anode and cathode are arranged in a concentric manner with a space between the anode and cathode, said anode is a ferrite pole with a hole along center axis and is filled with a connection part and comprises a connection part and a conductive terminal main body;

said connection part is pipe shaped and comprises soft, conductive metal with a low melting point;

said conductive terminal main body is inserted into the connection part; and a solution containing halogen ions is passed through the gap and electrolyzed.

2. An electrolyzer according to claim 1, wherein said anode is a ferrite pipe.

3. An electrolyzer according to claim 1, wherein said terminal main body has a screw thread and is screwed into the connection part.

4. An electrolyzer according to claim 1, wherein said connecting part comprises mercury.

5. An electrolyzer according to claim 1, wherein the terminal main body is inserted during the conductive part is heated and melted.

6. An electrolyzer according to claim 1, wherein said electrolyzer is arranged in a container and the solution is filled in the container.

7. An electrolyzer according to claim 6, wherein the solution is supplied in the gap and is electrolyzed until the solution reaches predetermined halogen concentration.

8. An electrolyzer according to claim 7, wherein said electrolyzer further comprises a sensor which measures concentration of the remaining halogen in the water in the container, and a controller which controls concentration of the remaining halogen in the water 9. An electrolyzer according to claim 6, wherein a plurality of electrolyzers is arranged in the container.

10. An electrolyzer according to claim 6, wherein said solution in the gap is lifted by air generated through electrolysis, discharged from an outlet within the container and introduced to the gap from an inlet opening within the container.

* * * * *